(12) United States Patent
Lebreton

(10) Patent No.: US 8,338,388 B2
(45) Date of Patent: *Dec. 25, 2012

(54) CROSS-LINKING OF LOW-MOLECULAR WEIGHT AND HIGH-MOLECULAR WEIGHT POLYSACCHARIDES, PREPARATION OF INJECTABLE MONOPHASE HYDROGELS, POLYSACCHARIDES AND HYDROGELS OBTAINED

(75) Inventor: Pierre Lebreton, Annecy (FR)

(73) Assignee: Allergan, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/782,488

(22) Filed: May 18, 2010

(65) Prior Publication Data

US 2010/0226988 A1 Sep. 9, 2010

Related U.S. Application Data

(62) Division of application No. 10/552,309, filed as application No. PCT/FR2004/000870 on Apr. 8, 2004, now Pat. No. 7,741,476.

(30) Foreign Application Priority Data

Apr. 10, 2003 (FR) ..................... 03 04444

(51) Int. Cl.
  *A01N 43/04* (2006.01)
  *A61K 31/715* (2006.01)
  *C08B 37/00* (2006.01)
  *C07H 5/04* (2006.01)
  *C07H 5/06* (2006.01)

(52) U.S. Cl. ........................ 514/54; 536/55.3

(58) Field of Classification Search .................. None
See application file for complete search history.

(56) References Cited

U.S. PATENT DOCUMENTS

| | | | |
|---|---|---|---|
| 2,128,827 A | 8/1938 | Killian |
| 3,548,056 A | 12/1970 | Eigen et al. |
| 3,763,009 A | 10/1973 | Suzuki |
| 3,949,073 A | 4/1976 | Daniels et al. |
| 4,060,081 A | 11/1977 | Yannnas et al. |
| 4,140,537 A | 2/1979 | Luck et al. |
| 4,233,360 A | 11/1980 | Luck et al. |
| 4,273,705 A | 6/1981 | Kato |
| 4,279,812 A | 7/1981 | Cioca |
| 4,424,208 A | 1/1984 | Wallace et al. |
| 4,501,306 A | 2/1985 | Chu et al. |
| 4,582,640 A | 4/1986 | Smestad et al. |
| 4,582,865 A | 4/1986 | Balazs et al. |
| 4,605,691 A | 8/1986 | Balazs et al. |
| 4,636,524 A | 1/1987 | Balazs |
| 4,642,117 A | 2/1987 | Nguyen et al. |
| 4,713,448 A | 12/1987 | Balazs |
| 4,716,154 A | 12/1987 | Malson et al. |
| 4,803,075 A | 2/1989 | Wallace et al. |
| 4,886,787 A | 12/1989 | de Belder et al. |
| 4,896,787 A | 1/1990 | Delamour et al. |
| 5,009,013 A | 4/1991 | Wiklund |
| 5,087,446 A | 2/1992 | Suzuki et al. |
| 5,091,171 A | 2/1992 | Yu et al. |
| 5,143,724 A | 9/1992 | Leshchiner et al. |
| 5,246,698 A | 9/1993 | Leshchiner et al. |
| 5,314,874 A | 5/1994 | Miyata et al. |
| 5,328,955 A | 7/1994 | Rhee et al. |
| 5,356,883 A | 10/1994 | Kuo et al. |
| 5,399,351 A | 3/1995 | Leshchiner et al. |
| 5,428,024 A | 6/1995 | Chu et al. |
| 5,531,716 A | 7/1996 | Luzio et al. |
| 5,565,519 A | 10/1996 | Rhee et al. |
| 5,571,503 A | 11/1996 | Mausner |
| 5,614,587 A | 3/1997 | Rhee et al. |
| 5,616,568 A | 4/1997 | Pouyani et al. |
| 5,616,611 A | 4/1997 | Yamamoto |
| 5,616,689 A | 4/1997 | Shenoy et al. |
| 5,633,001 A | 5/1997 | Agerup |
| 5,643,464 A | 7/1997 | Rhee et al. |
| 5,676,964 A | 10/1997 | della Valle |
| 5,823,671 A | 10/1998 | Mitchell et al. |
| 5,824,333 A | 10/1998 | Scopelianos et al. |
| 5,827,529 A | 10/1998 | Ono et al. |
| 5,843,907 A | 12/1998 | Sakai |
| 5,886,042 A | 3/1999 | Yu et al. |
| 5,935,164 A | 8/1999 | Iversen |
| 5,980,930 A | 11/1999 | Fenton et al. |

(Continued)

FOREIGN PATENT DOCUMENTS

CA        949 965        6/1974

(Continued)

OTHER PUBLICATIONS

Desai, et al., J Pharm Sci Feb. 1995; 84 (2): 212-5, abstract only.
Database Biosis, Biosciences Information Service, Philadelphia, PA, US, "Antiibrosis Effect of Novel Gels in Anterior Ciliary Slerotomy (ACS)", Accession No. PREV200300142886, 2 pp.
F.H. Silver, et al., "Physical Properties of Hyaluronic Acid and Hydroxypropylmethylcellulose in Solution: Evaluation of Coating Ability," Journal of Applied Biomaterials, vol. 5, 89-98 (1994).
GinShiCel MH Hydroxy Propyl methyl Cellulose, Web Page http://www.ginshicel.cn/MHPC.html, Nov. 12, 2008.
Hassan, HG., et al., Effects of Adjuvants to local anaesthetics on their duration. III. Experimental studies of hyaluronic acid. Abstract Pub Med [Acta Anesthesiol Scand. May 1985;29(4):384-8].
Sannino, et al., "Crosslinking of Cellulose Derivatives and Hyaluronic Acid With Water-Soluble Carbodimide," Polymer 46 (2005) 11206-11212 pp.

(Continued)

*Primary Examiner* — Layla Bland
(74) *Attorney, Agent, or Firm* — Linda Allyson Fox; Stephen Donovan; Debra Condino

(57) ABSTRACT

A process for the crosslinking of at least one polymer selected from polysaccharides and derivatives thereof, which is carried out in an aqueous solvent by the action of an effective and non-excessive amount of at least one crosslinking agent, characterized in that it is carried out on a mixture containing at least one low-molecular weight polymer and at least one high-molecular weight polymer. A process for the preparation of an injectable monophase hydrogel of at least one crosslinked polymer selected from polysaccharides and derivatives thereof. Crosslinked polymers and injectable monophase hydrogels respectively obtainable by each of said processes.

13 Claims, 1 Drawing Sheet

U.S. PATENT DOCUMENTS

| | | |
|---|---|---|
| 6,013,679 A | 1/2000 | Kuo et al. |
| 6,066,325 A | 5/2000 | Wallace et al. |
| 6,224,857 B1 | 5/2001 | Romeo et al. |
| 6,335,035 B1 | 1/2002 | Drizen et al. |
| 6,372,494 B1 | 4/2002 | Naughton et al. |
| 6,383,218 B1 | 5/2002 | Sourdille et al. |
| 6,383,219 B1 | 5/2002 | Telandro et al. |
| 6,418,934 B1 | 7/2002 | Chin |
| 6,521,223 B1 | 2/2003 | Calias et al. |
| 6,544,503 B1 | 4/2003 | Vanderhoff et al. |
| 6,627,620 B1 | 9/2003 | Nielsen |
| 6,630,486 B1 | 10/2003 | Royer |
| 5,880,107 A1 | 11/2003 | Khan |
| 6,685,963 B1 | 2/2004 | Taupin et al. |
| 6,716,251 B1 | 4/2004 | Asius et al. |
| 6,734,298 B1 | 5/2004 | Barbucci |
| 6,767,924 B2 | 7/2004 | Yu et al. |
| 6,767,928 B1 | 7/2004 | Murphy et al. |
| 6,852,255 B2 | 2/2005 | Yang |
| 6,893,466 B2 | 5/2005 | Trieu |
| 6,903,199 B2 | 6/2005 | Moon |
| 6,921,819 B2 | 7/2005 | Piron et al. |
| 6,924,273 B2 | 8/2005 | Pierce |
| 6,939,562 B2 | 9/2005 | Spiro et al. |
| 6,979,440 B2 | 12/2005 | Shefer et al. |
| 7,119,062 B1 | 10/2006 | Alvis et al. |
| 7,166,570 B2 | 1/2007 | Hunter et al. |
| 7,192,984 B2 | 3/2007 | Berg |
| 7,196,180 B2 | 3/2007 | Aeschlimann |
| 7,314,636 B2 | 1/2008 | Caseres et al. |
| 7,491,709 B2 | 2/2009 | Carey |
| 7,741,476 B2 | 6/2010 | Lebreton |
| 7,902,171 B2 | 3/2011 | Reinmuller et al. |
| 8,124,120 B2 | 2/2012 | Sadozai |
| 2002/0102311 A1 | 8/2002 | Gustavsson et al. |
| 2002/0160109 A1 | 10/2002 | Yeo et al. |
| 2003/0031638 A1 | 2/2003 | Joshi et al. |
| 2003/0093157 A1 | 5/2003 | Casares et al. |
| 2003/0119985 A1 | 6/2003 | Sehl et al. |
| 2003/0148995 A1 | 8/2003 | Piron et al. |
| 2004/0032056 A1 | 2/2004 | Vang et al. |
| 2004/0101959 A1 | 5/2004 | Marko et al. |
| 2004/0127698 A1 | 7/2004 | Tsai et al. |
| 2004/0127699 A1 | 7/2004 | Zhao et al. |
| 2004/0199241 A1 | 10/2004 | Gravett et al. |
| 2004/0265389 A1 | 12/2004 | Yui et al. |
| 2005/0101582 A1 | 5/2005 | Lyons et al. |
| 2005/0136122 A1 | 6/2005 | Sadozai et al. |
| 2005/0142152 A1 | 6/2005 | Leshchiner et al. |
| 2005/0181007 A1 | 8/2005 | Hunter |
| 2005/0186261 A1 | 8/2005 | Avelar |
| 2005/0227936 A1 | 10/2005 | Agerup |
| 2005/0271729 A1 | 12/2005 | Wang |
| 2005/0287180 A1 | 12/2005 | Chen |
| 2006/0040894 A1 | 2/2006 | Hunter et al. |
| 2006/0095137 A1 | 5/2006 | Chung et al. |
| 2006/0122147 A1 | 6/2006 | Wohlrab |
| 2006/0141049 A1 | 6/2006 | Lyons et al. |
| 2006/0147483 A1 | 7/2006 | Chaouk et al. |
| 2006/0194758 A1 | 8/2006 | Lebreton |
| 2006/0246137 A1 | 11/2006 | Hermitte et al. |
| 2006/0257488 A1 | 11/2006 | Hubbard |
| 2006/0286769 A1 | 12/2006 | Tsuchiya et al. |
| 2007/0026070 A1 | 2/2007 | Vonwiller et al. |
| 2007/0066816 A1 | 3/2007 | Tsai et al. |
| 2007/0077292 A1 | 4/2007 | Pinsky |
| 2007/0203095 A1 | 8/2007 | Sadozai et al. |
| 2007/0212385 A1 | 9/2007 | David |
| 2007/0224247 A1 | 9/2007 | Chudzik |
| 2007/0224278 A1 | 9/2007 | Lyons et al. |
| 2007/0298005 A1 | 12/2007 | Thibault |
| 2008/0044476 A1 | 2/2008 | Lyons et al. |
| 2008/0057091 A1 | 3/2008 | Abdellaoui |
| 2008/0089918 A1 | 4/2008 | Lebreton |
| 2008/0188416 A1 | 8/2008 | Bernstein |
| 2008/0193538 A1 | 8/2008 | Kitazono et al. |
| 2008/0200430 A1 | 8/2008 | Bitterman et al. |
| 2008/0207794 A1 | 8/2008 | Wright et al. |
| 2008/0241252 A1 | 10/2008 | Lyons |
| 2008/0268051 A1 | 10/2008 | Lyons |
| 2008/0274946 A1 | 11/2008 | Gimpapa |
| 2008/0279806 A1 | 11/2008 | Cho |
| 2009/0018102 A1 | 1/2009 | Moutet |
| 2009/0022808 A1 | 1/2009 | Champion |
| 2009/0028817 A1 | 1/2009 | Niklason et al. |
| 2009/0036403 A1 | 2/2009 | Stroumpoulis et al. |
| 2009/0042834 A1 | 2/2009 | Karageozian et al. |
| 2009/0093755 A1 | 4/2009 | Schroeder |
| 2009/0110671 A1 | 4/2009 | Miyata et al. |
| 2009/0110736 A1 | 4/2009 | Boutros |
| 2009/0143331 A1 | 6/2009 | Stroumpoulis et al. |
| 2009/0143348 A1 | 6/2009 | Tezel |
| 2009/0148527 A1 | 6/2009 | Robinson |
| 2009/0155314 A1 | 6/2009 | Tezel |
| 2009/0155362 A1 | 6/2009 | Longin |
| 2009/0169615 A1 | 7/2009 | Pinsky |
| 2009/0291986 A1 | 11/2009 | Pappas et al. |
| 2009/0297632 A1 | 12/2009 | Waugh |
| 2010/0004198 A1 | 1/2010 | Stroumpoulis et al. |
| 2010/0028437 A1 | 2/2010 | Lebreton |
| 2010/0035838 A1 | 2/2010 | Heber et al. |
| 2010/0041788 A1 | 2/2010 | Voigts et al. |
| 2010/0098764 A1 | 4/2010 | Stroumpoulis et al. |
| 2010/0098794 A1 | 4/2010 | Armand |
| 2010/0099623 A1 | 4/2010 | Schroeder et al. |
| 2010/0111919 A1 | 5/2010 | Abuzaina et al. |
| 2010/0136070 A1 | 6/2010 | Dobak et al. |
| 2010/0226988 A1 | 9/2010 | Lebreton |
| 2010/0316683 A1 | 12/2010 | Piron |
| 2011/0034684 A1 | 2/2011 | Yokokawa |

FOREIGN PATENT DOCUMENTS

| | | |
|---|---|---|
| EP | 0273823 | 7/1988 |
| EP | 0416250 A2 | 3/1991 |
| EP | 0416846 | 3/1991 |
| EP | 1247522 | 10/2002 |
| EP | 1419792 | 4/2003 |
| EP | 1398131 | 3/2004 |
| EP | 1726299 | 11/2006 |
| EP | 2236523 | 10/2010 |
| FR | 2733427 | 10/1996 |
| FR | 2920000 | 2/2009 |
| FR | 2924615 | 6/2009 |
| JP | 55-153711 | 11/1980 |
| JP | 2007063177 | 3/2007 |
| WO | WO86/00079 A1 | 1/1986 |
| WO | WO86/00912 A1 | 2/1986 |
| WO | WO 92/00105 | 1/1992 |
| WO | WO 92/20349 A1 | 11/1992 |
| WO | WO 94/01468 | 1/1994 |
| WO | WO 94/02517 A1 | 2/1994 |
| WO | WO 96/33751 | 1/1996 |
| WO | WO 97/04012 | 2/1997 |
| WO | 9835639 | 8/1998 |
| WO | 9835640 | 8/1998 |
| WO | 0001428 | 1/2000 |
| WO | WO 01/79342 | 10/2001 |
| WO | WO 02/05753 | 1/2002 |
| WO | WO 02/06350 | 1/2002 |
| WO | WO02/09792 A1 | 2/2002 |
| WO | WO 02/17713 | 3/2002 |
| WO | WO03/007782 | 1/2003 |
| WO | WO 2004/020473 | 3/2004 |
| WO | WO 2004/022603 | 3/2004 |
| WO | WO 2004/073759 | 9/2004 |
| WO | WO 2004/092223 | 10/2004 |
| WO | WO 2005/040224 | 5/2005 |
| WO | WO2005/067994 A1 | 7/2005 |
| WO | WO 2005/074913 | 8/2005 |
| WO | WO2005/112888 A | 12/2005 |
| WO | WO 2006/023645 | 3/2006 |
| WO | WO 2006/067608 | 6/2006 |
| WO | WO 2007/018124 | 2/2007 |
| WO | WO 2007/070617 | 6/2007 |
| WO | WO 2007/077399 | 7/2007 |
| WO | WO 2007/128923 | 11/2007 |
| WO | WO 2008/034176 | 3/2008 |

| | | |
|---|---|---|
| WO | WO 2008/068297 | 6/2008 |
| WO | WO 2008/072230 | 6/2008 |
| WO | WO 2008/077172 | 7/2008 |
| WO | WO 2008/098019 | 8/2008 |
| WO | WO 2008/139122 | 11/2008 |
| WO | WO 2008/148967 | 12/2008 |
| WO | WO 2008/157608 | 12/2008 |
| WO | WO 2009/024719 | 2/2009 |
| WO | WO 2009/026158 | 2/2009 |
| WO | WO 2009/028764 | 3/2009 |
| WO | WO 2009/034559 | 3/2009 |
| WO | WO 2009/073437 | 6/2009 |
| WO | WO 2010/003797 | 1/2010 |
| WO | WO 2010/015900 | 2/2010 |
| WO | WO 2010/027471 | 3/2010 |
| WO | WO 2010/028025 | 3/2010 |
| WO | WO 2010-029344 | 3/2010 |
| WO | WO 2010-038771 | 4/2010 |
| WO | WO 2010/051641 | 5/2010 |
| WO | WO 2010/052430 | 5/2010 |
| WO | WO 2010/053918 | 5/2010 |
| WO | WO 2010/061005 | 6/2010 |

OTHER PUBLICATIONS

Kulicke, et al., "Visco-Elastic Properties of Sodium Hyaluronate Solutions," American Institute of Physics (2008).

Tezel, "The Science of Hyaluroinic Acid Dermal Fillers Journal of Cosmetic and Laser Therapy," (2008) 10:34-42 pp.

LUPO, "Hyaluronic Acid Fillers in Facial Rejuvenation", Seminars in Cutaneous Medicine and Surgery, Oct. 18, 2006, vol. 25, Issue 3, pp. 122-126.

*Aesthetic Buyers Guide,* "Juvéderm Raises Standards"; Jan./Feb. 2007 (5 pp.), www.miinews.com.

Adams; "An Analysis of Clinical Studies of the Uses of Crosslinked Hyaluronan, Hylan, in the Treatment of Osteoarthritis"; J. Rheumatol Suppl. ; vol. 39; pp. 16-18; Aug. 1993.

Albano et al.; "Hyroxyethyl Radicals in Ethanol Hepatotoxicity"; Frontiers in Bioscience; vol. 4; pp. 533-540; 1999.

Allemann et al.; "Hyaluronic acid gel (JUVADERM) preparations in the treatment of facial wrinkles and folds"; Clinical Interventions in Aging; vol. 3, No. 4; pp. 629-634; 2008.

Antunes et al.; "Efficacy of Intrarectal Lidocaine Hydrochloride Gel for Pain control in Patients Undergoing Transrectal Prostate Biopsy"; International Braz J Urol; vol. 30, No. 5; pp. 380-383; Sep.-Oct. 2004.

Atanassoff et al.; "The Effect of Intradermal Administration of Lidocaine and Morphine on the Response to Thermal Stimulation"; Anesth Analg; vol. 84; pp. 1340-1343; 1997.

Baumann et al.; "Comparison of smooth-gel hyaluronic acid dermal fillers with cross-linked bovine collagen: a multicenter, double-masked, randomized, within-subject study"; Dermatol. Surg.; vol. 33(Suppl 2); pp. S128-S135 2007.

Beasley et al.; "Hyaluronic acid fillers: a comprehensive review"; Facial Plast. Surg.; vol. 25, No. 2; pp. 86-94; 2009.

Beer; "Dermal fillers and combinations of fillers for facial rejuvenation"; Dermatol. Clin.; vol. 27, No. 4; pp. 427-432; 2009.

Belda et al.; "Hyaluronic acid combined with mannitol to improve protection against free-radical endothelial damage: Experimental Model"; J.Cataract Refract Surg; Vo. 31; pp. 1213-1218; 2005.

Bircher, et al.; "Delayed-Type Hypersensitivity to Subcutaneous Lidocaine With Tolerance to Articaine: Confirmation by in Vivo and in Vitro Tests"; Contact Dermatitis; vol. 34; pp. 387-389; 1996.

Bluel et al.; "Evaluation of Reconstituted Collagen Tape as a Model for Chemically Modified Soft Tissues", Biomat. Med. Dev. Art. Org.; vol. 9(1); pp. 37-46; 1981.

Capozzi et al., "Distant Migration of Silicone Gel From a Ruptured Breast Implant", Plastic and Reconstructive Surgery; vol. 62; pp. 302-303; 1978.

Carlin et al., "Effect of anti-inflammatory drugs on xanthine oxidase and xanthine oxidase induced depolymerization of hyaluronic acid"; Agents and Actions; vol. 16 (5); pp. 377-384; 1985.

Carruthers et al.; "The science and art of dermal fillers for soft-tissue augmentation"; J. Drugs Dermatol; vol. 8(4); pp. 335-350; 2009.

Champion et al., "Role of Target Geometry in Phagocytosis"; S. Proc. Nat. Acad. Sci.; vol. 103; No. 13; pp. 4930-4934; Mar. 28, 2006.

Chin et al., "Allergic Hypersensitivity to Lidocaine Hydrochloride", International journal of Dermatology, vol. 19; pp. 147-148; Apr. 1980.

Chvapil, "Collagen Sponge: Theory and Practice of Medical Applications", J. Biomed Mater. Res., vol. II, pp. 721-741; 1977.

Clark et al., "The Influence of Triamcinolone Acetonide on Joint Stiffness in the Rat", J Bone Joint Surg; vol. 53-A; pp. 1409-1414; Oct. 1971.

Cohen et al., "Organization and Adhesive Properties of the Hyaluronan Pericellular Coat of Chrondrocytes and Epithelial Cells", Biophys J.; vol. 85; pp. 1996-2005; Sep. 2003.

Deland, "Intrathecal Toxicity Studies with Benzyl Alcohol", Toxicol Appl Pharmacol; vol. 25; pp. 153-156; 1973.

Eyre et al., Top Curr. Chem., vol. 247, pp. 207-229; 2005.

Falcone et al.; "Crosslinked hyaluronic acid dermal fillers: a comparison of rheological properties." J Biomed Mater Res; vol. 87(1); pp. 264-271; 2008.

Falcone et al.; "Temporary polysaccharide dermal fillers: a model for persistence based on physical properties." Dermatol Surg.; vol. 35(8); pp. 1238-1243; 2009.

Farley et al., "Diluting Lidocaine and Mepivacaine in Balanced Salt Solution Reduces the Pain of Intradermal Injection", Regional Anesthesia; vol. 19(1); pp. 48-51; 1994.

Frati et al., "Degradation of hyaluronic acid by photosensitized riboflavin in vitro. Modulation of the effect by transition metals, radical quenchers, and metal chelators"; Free Radical Biology Medicine; vol. 22 (7); pp. 1139-1144 1997.

Fujinaga et al., "Reproductive and Teratogenic Effects of Lidocaine in Sprague-Dawley Rats"; Anesthesiology vol. 65; pp. 626-632; 1986.

Gammaitoni et al., "Pharmacokinetics and safety of continuously applied lidocaine patches 5%", Am J Health Syst Pharm; vol. 59; pp. 2215-2220; Nov. 15, 2002.

Gold; "Use of Hyaluronic acid fillers for the treatment of the aging face"; Clin. Interventions Aging; vol. 2(3); pp. 369-376; 2007.

Goldberg; "Breakthroughs in US dermal fillers for facial soft-tissue augmentation"; J Cosmet Laser Ther; vol. 11; pp. 240-247; 2009.

Graefe et al., "Sensitive and specific photometric determination of mannitol in human serum"; Clin Chem Lab Med; vol. 41, No. 8; pp. 1049-1055; 2003.

Grecomoro et al., "Intra-Articular Treatment with Sodium Hyaluronate in Gonarthosis: A Controlled Clinical Trial Versus Placebo", Pharmatherapeutica, vol. 5(2); pp. 137-141; 1987.

Grillo et al., "Thermal Reconstitution of Collagen from Solution and the Response to Its Heterologous Implantation", JSR; vol. II, No. 1, pp. 69-82; Jan. 1962.

Hayashibara, "AA2G"; Sep. 23, 2007, http://web.archive.org/web/20079230720 10/http://www.hayashibara-intl.com/cosmetics/aa2g.html.

Helliwell, "Use of an Objective Measure of Articular Stiffness to Record Changes in Finger Joints After Intra-Articular Injection of Corticosteroid", An Theum Dis; vol. 56; pp. 71-73; 1997.

Hertzberger-Ten Cate et al., "Intra-Articular Steroids in Pauciarticular Juvenile Chronic Arthritis", Type I, Eur J Pediatr; vol. 150; pp. 170-172; 1991.

Hetherington, "Potential for Patient Harm From Intrathecal Administration of Preserved Solutions", Abstract only Med J; vol. 173(3); p. 141; Aug. 2000.

Hurst, "Adhesive Arachnoiditis and Vascular Blockage Caused by Detergents and Other Chemical Irritants: an Experimental Study", J Path Bact, vol. LXX, No. 70; pp. 167-177; 1955.

Intramed Mannitol 20% m/v Infusion, package insert, pp. 1-2 (2010) http://home.intekom.com/pharm/intramed/manitI20.html.

Jones et al., "Intra-Articular Hyaluronic Acid Compared to Intra-Articular Triamcinolone Hexacetonide in Inflammatory Knee Osteoarthritis", Osteoarthritis Cartilage, vol. 3; pp. 269-273; 1995.

Kablik et al. "Comparative physical properties of hyaluronic acid dermal fillers." Dermatol. Surg.; vol. 35(Suppl. 1); pp. 302-312; 2009.

Klein, "Skin Filling Collagen and Other Injectables of the Skin", Dermatologic Clinics; vol. 19, No. 3, pp. 491-588; Jul. 2001.

Kopp et al., "The Short-Term Effect of Intra-Articular Injections of Sodium Hyaluronate and Corticosteroid on Temporomandibular Joint Pain and Dysfunction"; J. Oral Maxillofac Surg.; V. 43; pp. 429-435; 1985.

Laeschke, "Biocompatibility of Microparticles into Soft Tissue Fillers", Semin. Cutan. Med. Surg., vol. 23; pp. 214-217; 2004.

Levy et al., "Lidocaine hypersensitivity after subconjunctival injection", Can J Ophthalmol 2006; vol. 41, No. 2; pp. 204-206.

Mackley et al., "Delayed-Type Hypersensitivity to Lidocaine", Arch Dermatol, vol. 139; pp. 343-346; Mar. 2003.

Mancinelli et al., "Intramuscular High-Dose Triamcinolone Acetonide in the Treatment of Severe Chronic Asthma", West J. Med; vol. 167(5); pp. 322-329; Nov. 1997.

Matsumoto et al., "Reducing the Discomfort of Lidocaine Administration through pH Buffering," Journal of Vascular and Interventional Radiology; vol. 5, No. 1; pp. 171-175; Nov. 1997.

McCarty et al., "Inflammatory Reaction After Intrasynovial Injection of Microcrystalline Adrenocorticosteroid Esters", Arthritis and Rheuymatism; vol. 7(4); pp. 359-367; 1964.

McCleland et al.; "Evlaution of Artecoll Polymethacrylate Implant for Soft-Tissue Augmentation: Biocompatibility and Chemical Chartacterization"; Plastric Reconstructive Surgery; vol. 100(6); pp. 1466-1474; Nov. 1997.

McPherson et al; "Development and Biochemical Characterization of Injectable Collagen," J. Dermatol Surg Oncol; vol. 14 (Suppl1); pp. 13-20; Jul. 7, 1988.

Orvisky et al., "High-molecular-weight hyaluronan—a valuable tool in testing the antioxidative activity of amphiphilic drugs stobadine and vinpocetine"; J. Pharm. Biomed. Anal.; vol. 16; pp. 419-424; 1997.

Osmitrol (generic name Mannitol),Official FDA Information, side effects and uses, pp. 1-10 (2010) http://www.drugs.com/pro/osmitrol.html.

Prestwich; "Evaluating drug efficacy and toxicology in three dimensions: using synthetic extracellular matrices in drug discovery"; Accounts of Chemical Research; vol. 41, No. 1; pp. 139-148; Jan. 2008.

Rehakova et al.; "Properties of collagen and hyaluronic acid composite materials and their modifications by chemical crosslinking," Journal of Biomedical Materials Research; vol. 30; pp. 369-372; 1996.

Remington's Pharmaceutical Science Mac Publishing Company, Easton, PA 16th Edition 1980; 1-page.

Rosenblatt et al., "The Effect of Collagen Fiber Size Distribution on the Release Rate of Proteins from Collagen Matrices by Diffusion", J. Controlled Rel., vol. 9; pp. 195-203; 1989.

Rosenblatt et al., "Chain Rigidity and Diffusional Release in Biopolymer Gels", Proceed. Inter. Symp. Control. Rel. Bioact. Mater.; vol. 20; pp. 264-265; 1993; Controlled Release Society, Inc.

SCULPTRA® Aesthetic (injectable poly-L-lactic acid) Directions for Use, Dermik Laboratories product insert (Jul. 2009), sanofi-aventis U.S. LLC; 10 pages.

Segura et al. "Crosslinked hyaluronic acid hydrogels: a strategy to functionalize and pattern." Biomaterials; vol. 26; pp. 359-371; 2005.

Selvi et al, "Arthritis Induced by Corticosteroid Crystals", J. Rheumatology; vol. 34:3; 1 page; 2004.

Serban et al., "Modular Extracellular Matrices: Solutions for the Puzzle"; Methods; vol. 45(1)pp. 93-98; 2008.

Shu et al., "Synthesis and evaluation of injectable, in situ crosslinkable synthetic extracellular matrices for tissue engineering"; J. Biomed. Mater. Res. A.; vol. 79(4); pp. 902-912; 2006.

Smith et al., "Five Percent Lidocaine Cream Applied Simultaneously to Skin and Mucosa of the Lips Creates Excellent Anesthesia for Filler Injections", Dermatol Surg; vol. 31; pp. 1635-1637; 2005.

TRB Chemedica Ophthalmic Line, Visiol, product info., pp. 1-2; No date.

VISIOL, Viscoelstic gel for use in ocular surgery, (2010) p. 1, htt://www.trbchemedica.com/index.php/option=com_content&tas.

Waraszkiewicz et al., "Stability-Indicating High-Performance Liquid Chromatographic Analysis of Lidocaine Hydrochloride and Lidocaine Hydrochloride with Epinephrine Injectable Solutions", Journal of Pharmaceutical Sciences, vol. 70, No. 11, pp. 1215-1218, Nov. 1981.

Xia et al., "Comparison of Effects of Lidocaine Hydrochloride, Buffered Lidocaine, Diphenhydramine, and Normal Saline After Intradermal Injection", Journal of Clinical Anesthesia 14:339-343, 2002.

Yeom et al., "Effect of Cross-Linking Reagents for Hyaluronic Acid Hydrogel Dermal Fillers on Tissue Augmentation and Regeneration", Bioconjugate Chem., vol. 21; pp. 240-247; 2010.

Yui, et al., "Inflammation responsive degradation of crosslinked hyaluronic acid gels," Journal of Controlled Release, vol. 22; pp. 105-116; 1992.

Yui et al., "Photo-responsive degradation of heterogeneous hydrogels comprising crosslinked hyaluronic acid and lipid microspheres for temporal drug delivery," Journal of Controlled Release; vol. 26; pp. 141-145; 1993.

Yun et al., "Hyaluronan Microspheres for Sustained Gene Delivery and Site-Specific Targeting", Biomaterials, vol. 25, pp. 147-157, 2004.

Zheng Shu et al., "In situ crosslinkable hyaluronan hydrogels for tissue engineering." Biomaterials; vol. 25; pp. 1339-1348; 2004.

Zulian et al., "Triamcinolone Acetonide and Hexacetonide Intra-Articular Treatment of Symmetrical Joints in Juvenile Idiopathic Arthritis: a Double-Blind Trial", Rheumatology; vol. 43; No. 10; pp. 1288-1291; 2004.

Powell; "Stability of Lidocaine in Aqueous Solution: Effect of Temperature, pH, Buffer, and Metal Ions on Amide Hydrolysis"; Pharmaceutical Research; vol. 4, No. 1, 1987.

Cui et al; "The Comparison of Physicochemical Properties of Four Cross-Linked Sodium Hyaluronate Gels with Different Cross-Linking Agents"; Advanced Material Research; vols. 396-398; pp. 1506-1512; 2012.

Lindvall et al.; "Influence of Various Compounds on the Degradation of Hyaluronic Acid by a Myeloperoxidase System"; Chemcio-Biological Interactions; vol. 90; pp. 1-12; 1994.

Weidmann; "New Hyaluronic Acid Filler for Subdermal and Long-Lasting Volume Restoration of the Face"; European Dermatology; pp. 65-68; 2009.

Skardal etal "Bioprinting Vessel-Like Constructs Using Hyaluronan Hydrogels Crosslinkedwith Tetrahedral Polyethylene Glyol Tetracrylates"; BioMaterials. Elsevier Science Publishers BV; vol. 31, No. 24; pp. 6173-6181; Aug. 1, 2010.

Millay et al.; "Vasoconstrictors in Facial Plastic Surgery"; Archives of Otolaryngology-Head & Neck Surgery; vol. 117; pp. 160-163; Feb. 1991.

Wahl, "European Evaluation of a New Hyaluronic Acid Filler Incorporating Lidocaine", Journal of Cosmetic Dermatology; vol. 7; pp. 298-303; 2008.

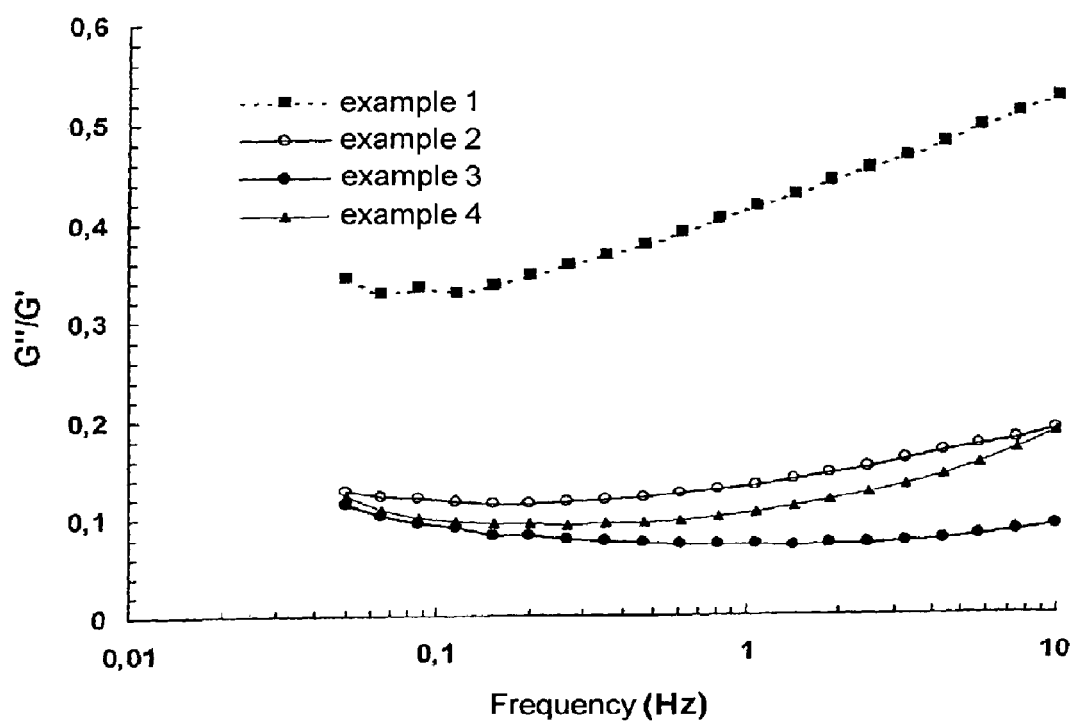

CROSS-LINKING OF LOW-MOLECULAR WEIGHT AND HIGH-MOLECULAR WEIGHT POLYSACCHARIDES, PREPARATION OF INJECTABLE MONOPHASE HYDROGELS, POLYSACCHARIDES AND HYDROGELS OBTAINED

CROSS REFERENCE TO RELATED APPLICATIONS

This application is a divisional of U.S. patent application Ser. No. 10/552,309, filed Oct. 7, 2005, which is a U.S. national phase application of PCT No. PCT/FR04/00870, filed Apr. 8, 2004, which claims priority from French patent application No. 030444, filed Apr. 10, 2003.

BACKGROUND OF THE INVENTION

1. Field of the Invention

The present invention relates to:
a novel process for the crosslinking of at least one polymer selected from polysaccharides and derivatives thereof;
a process for the preparation of an injectable monophase hydrogel of at least one such polymer; and
the crosslinked polymers and injectable monophase hydrogels respectively obtainable by each of said processes.

2. Description of the Related Art

The hydrogels in question, based on said crosslinked polymers, have numerous outlets, especially as filling materials in plastic, cosmetic and dental surgery, in ophthalmology, in orthopedics, etc., as products for preventing tissue adhesions, in general surgery, in urology, etc. Said hydrogels are particularly suitable for repairing vocal cords. The outlets indicated above for products of this type, without implying any limitation, are familiar to those skilled in the art.

The invention is the result of a genuine effort to optimize the operation of crosslinking the polymers in question with a view to obtaining injectable monophase hydrogels that are of particular value in respect of the following compromise: on the one hand mechanical properties and remanence, and on the other hand injectability (with acceptable injection forces and injection needle diameters).

It is pointed out here that the term "injectable" employed in the present text, with reference to both the hydrogels of the prior art and the hydrogels of the invention, denotes manual injectability by means of syringes equipped with conventional needles (having a diameter of between 0.1 and 0.5 mm). Within the framework of the present invention, it is possible in particular to formulate hydrogels that can be injected through hypodermic needles of 30 G½, 27 G½, 26 G½ and 25 G.

According to the prior art, hydrogels, especially injectable hydrogels, have already been prepared from polysaccharides and derivatives thereof—especially hyaluronic acid salts—having a zero, low or high degree of crosslinking.

With reference to the specific problem of injectability, biphase compositions have been proposed whose continuous phase, in particular, is based on such hydrogels. The continuous phase serves as a plasticizer, injection vehicle for a disperse phase. This disperse phase is more or less solid and more or less differentiated from the continuous phase. Thus:

the biphase compositions described in patent application EP-A-0 466 300 consist of two bioabsorbable phases—continuous and disperse—and take the form of slurries. Said two phases are advantageously prepared from fibers of Hylan (natural hyaluronic acid chemically modified in situ in order to facilitate its extraction from the tissues);

the biphase compositions described in patent application WO-A-96 337 51 also have two bioabsorbable phases with a better separation, the disperse phase consisting of insoluble fragments of a highly crosslinked polymer hydrogel (selected from hyaluronic acid and its salts);

the biphase compositions described in patent application WO-A-00 014 28 contain a non-bioabsorbable disperse phase (particles of at least one hydrogel of a (co)polymer obtained by the polymerization and crosslinking of acrylic acid and/or methacrylic acid and/or at least one derivative of said acids) suspended in an aqueous solution of a crosslinked or non-crosslinked polymer selected from proteins, polysaccharides and derivatives thereof.

These biphase systems are not fully satisfactory insofar as they are associated with justifiable fears of uneven flow during injection and particularly after injection, a more rapid disappearance of the continuous phase (having a zero or low degree of crosslinking) and hence an at least partial loss of the desired effect, especially filling effect.

Monophase hydrogels, developed from the same types of polymers, were therefore also proposed in parallel.

In patent applications WO-A-98 356 39 and WO-A-98 356 40, the product in question is not an injectable hydrogel but a product of solid consistency. Said patent applications in fact describe ocular implants used to temporarily fill a surgically created void. The hydrogel developed in U.S. Pat. No. 4,716,154 is proposed as a substitute for the vitreous body. The polymer in question (sodium hyaluronate) has a very low degree of crosslinking in order to obtain an injectable hydrogel. The monophase hydrogel described in patent application WO-A-02 057 53 is laden with an antiseptic that is effective in protecting it from free radicals after implantation. Patent application WO-A-02 063 50 describes a process capable of generating this type of hydrogel that is very homogeneous throughout.

All these monophase hydrogels were obtained from high-molecular weight polymers crosslinked using an effective and non-excessive amount of at least one crosslinking agent, in an aqueous solvent.

SUMMARY OF THE INVENTION

In the light of this prior art, the inventors wished to improve the efficacy of crosslinking of the polymer in question, especially in order to improve the degradation resistance (remanence) of the implanted hydrogel while at the same time preserving the possibility of injecting said hydrogel under acceptable conditions.

To improve the crosslinking efficacy, the inventors initially considered using more crosslinking agent. This approach was quickly discarded on the grounds that it inescapably causes denaturation of the polymer in question and chemical contamination of the crosslinked product obtained.

Said inventors then considered increasing the concentration of polymer in the reaction mixture. In the same way, this second approach had to be discarded, a priori, because of the polymers conventionally used hitherto, namely high-molecular weight polymers. Thus sodium hyaluronate is always used with high molecular weights (Mw$\geq 10^6$ Da, $\approx 2.10^6$ Da, $3.10^6$ Da) at concentrations close to the maximum concentration, which is about 105-110 mg/g. Using it at a higher concentration is difficult (the viscosity of the reaction mixture becomes too high) and inescapably causes problems of solubility, poor homogeneity, etc.

Concentrating the reaction medium, on the other hand, is found to be possible with low-molecular weight polymers (sodium hyaluronate of molecular weight 300,000 Da, having an intrinsic viscosity of 600 ml/g (those skilled in the art are perfectly familiar with the relationship between these two parameters: molecular weight (M) and intrinsic viscosity ($\eta$), which is given by the Mark-Houwink formula: $M=k\eta^{\alpha}$, the values of k and $\alpha$ depending on the nature of the polymer in question), can be concentrated from 110 to 200 mg/g). Unfortunately the crosslinked polymer obtained generates an inhomogeneous, injectable biphase hydrogel under these conditions.

In such a context, the inventors surprisingly established that associating low-molecular weight polymer(s) with high-molecular weight polymer(s) affords an excellent compromise, namely the possibility of generating, for a non-excessive degree of crosslinking (equivalent to that of the prior art), an injectable monophase hydrogel which has improved mechanical and remanence properties. This low-molecular weight/high-molecular weight association makes it possible to obtain a hydrogel that more than satisfies the following specifications:
  monophase;
  better mechanical properties and remanence than the equivalent products of the prior art;
  unaffected or even improved injectability that is still possible with conventional injection forces using conventional injection devices.

The key factor of the crosslinking process of the invention therefore lies in the concentration of the reactants (which is greater than that of the reaction mixtures of the prior art due to the use of low-molecular weight polymer(s)), although the crosslinking of said concentrated reactants is "governed" by the use of high-molecular weight polymer(s), which guarantee the homogeneity of the crosslinked product obtained and then of the hydrogel obtained.

According to its first subject, the present invention therefore relates to a process for the crosslinking of at least one polymer selected from polysaccharides and derivatives thereof, which is carried out in an aqueous solvent by the action of an effective and non-excessive amount of at least one crosslinking agent, said process being improved in that it is carried out on a mixture containing at least one low-molecular weight polymer and at least one high-molecular weight polymer.

Said mixture of course contains said low-molecular weight polymer(s) in a sufficient amount to guarantee a relatively high concentration of polymer(s) in the reaction medium, and said high-molecular weight polymer(s) in a sufficient amount to guarantee that said crosslinked polymer obtained has a homogeneous consistency.

The crosslinking process of the invention is a process for the crosslinking of polymers selected from polysaccharides and derivatives thereof. The polymer(s) in question can therefore be natural or synthetic. Examples of natural polymers are hyaluronic acid and its salts, other glycosaminoglycans such as chondroitin sulfates, keratan sulfate, heparin and heparan sulfate, alginic acid and its biologically acceptable salts, starch, amylose, dextran, xanthan, pullulan, etc. Examples of synthetic derivatives of natural polysaccharides are carboxy cellulose, carboxymethyl cellulose, alkyl celluloses such as hydroxyethyl cellulose and hydroxypropyl methyl cellulose (HPMC), oxidized starch, etc.

The process of the invention is suitable for the crosslinking of any one of these polymers insofar as said polymer is used with low and high molecular weights.

The process of the invention is suitable for the crosslinking of mixtures of such polymers, said mixtures containing at least one low-molecular weight polymer and at least one high-molecular weight polymer.

The terms "low" and "high" applied to the molecular weights in question obviously cannot be defined more precisely at this stage of the description of the invention since they depend on the mixture in question and the nature of the polymer(s) present. Likewise, it is not generally possible to indicate the relative proportions in which the polymer(s) present is(are) used. However, those skilled in the art have a perfect understanding of the spirit of the invention, which is to concentrate the reaction medium containing the low-molecular weight polymer(s), but to introduce at least one high-molecular weight polymer to moderate and control the crosslinking in question. The aim is to obtain a coherent crosslinked product that is the precursor of a monophase hydrogel. It is desirable to avoid the formation of lumps that may be coherent when crosslinking has ended, but capable of losing their coherence when the injectable hydrogel is prepared.

The above explanations are given a posteriori. The result obtained was in no way predictable.

Within the framework of one advantageous variant, the reaction medium contains a single polymer which is used with at least two differentiated molecular weights, at least one being low and at least one being high. Within the framework of this advantageous variant, the same polymer is preferably used with a single low molecular weight and a single high molecular weight.

The polymer in question is advantageously a hyaluronic acid salt. It is very advantageously selected from the sodium salt, the potassium salt and mixtures thereof. It preferably consists of the sodium salt (NaHA).

In the context of the crosslinking of this type of polymer, those skilled in the art understand that said crosslinking is carried out in a basic aqueous solvent. In general, said crosslinking is obviously carried out under pH conditions that favor the dissolution of the polymer in question.

In the context of the crosslinking of this type of polymer (hyaluronic acid salt(s)), in one preferred variant of carrying out the crosslinking, the reaction mixture contains:
  at least one hyaluronic acid salt of low molecular weight m, where $m \leq 9.9 \cdot 10^5$ Da, advantageously $10^4$ Da $\leq m \leq 9.9 \cdot 10^5$ Da; and
  at least one hyaluronic acid salt of high molecular weight M, where $M \geq 10^6$ Da, advantageously $10^6$ Da $\leq M \leq 10^8$ Da and very advantageously $1.1 \cdot 10^6$ Da $\leq M \leq 5.10^6$ Da,
  said low-molecular weight and high-molecular weight salts advantageously being of the same nature and very advantageously consisting of sodium hyaluronate (NaHA).

In such a context, said reaction mixture advantageously has an intrinsic viscosity of less than 1900 ml/g, i.e. $\Sigma \omega_i [\eta_i]_0 < 1900$ ml/g, where $\omega_i$ is the mass fraction of polymer fraction i, having an intrinsic viscosity $[\eta_i]_0$, in the reaction mixture. Those skilled in the art are familiar with the intrinsic viscosity parameter and are aware of the laws of additivity of said parameter.

The condition stated above makes it possible to obtain a monophase hydrogel that is optimized in respect of its remanence and injectability properties. It fixes the relative proportions of the salts of low molecular weight (m) and high molecular weight (M).

In the context referred to here (NaHA of molecular weights m and M), the reaction mixture advantageously contains more than 50% by weight, very advantageously more than 70% by weight, of at least one hyaluronic acid salt of low molecular weight m, and hence, logically, advantageously less than 50% by weight, very advantageously less than 30% by weight, of at least one hyaluronic acid salt of high molecular weight M.

In general, to obtain the expected effect, there is at least 5% by weight of at least one hyaluronic acid salt of high molecular weight M in the reaction mixture.

The crosslinking process of the invention is advantageously carried out with the sodium salt of hyaluronic acid used with one low molecular weight m and one high molecular weight M, said parameters then very advantageously being as follows: $m \approx 3.10^5$ Da and $M \approx 3.10^6$ Da.

Any agent known for crosslinking polysaccharides and derivatives thereof via its hydroxyl groups can be used as the crosslinking agent with all types of polymer, said crosslinking agent being at least bifunctional in order to ensure crosslinking, an epoxy compound or derivatives thereof being used in particular.

It is recommended to use bifunctional crosslinking agents, by themselves or in a mixture. It is particularly recommended to use epichlorohydrin, divinyl sulfone, 1,4-bis(2,3-epoxypropoxy)butane (or 1,4-bisglycidoxybutane or 1,4-butanediol diglycidyl ether (BDDE)), 1,2-bis(2,3-epoxypropoxy)ethylene, 1-(2,3-epoxypropyl)-2,3-epoxycyclohexane, and aldehydes such as formaldehyde, glutaraldehyde and crotonaldehyde, taken by themselves or in a mixture. It is very particularly recommended to use 1,4-bis(2,3-epoxypropoxy)butane (BDDE).

Those skilled in the art will know how to determine the effective and non-excessive amount of crosslinking agent(s) to use. It is recommended to use an effective and non-excessive amount such that the degree of crosslinking ($\tau$), defined by the following ratio:

$$\tau = \frac{\text{Total number of reactive groups in said crosslinking agent}}{\text{Total number of disaccharide units in the polymer molecules}} \times 100,$$

is theoretically between 0.5 and 70%, advantageously between 4 and 50%.

The crosslinking process of the invention is novel by virtue of the forms in which the polymers in question are used. In other respects it is carried out in conventional manner with at least one crosslinking agent. It is noted that said crosslinking agent is generally reacted with the dissolved polymer(s), but reacting it with said polymer(s) during hydration, by the process described in WO-A-02 06 350, is in no way ruled out.

The crosslinked product obtained after carrying out the crosslinking process of the invention is generally formulated for generating the desired injectable monophase hydrogel. If necessary, it is neutralized beforehand. It has been seen that the hyaluronic acid salts are actually crosslinked in a basic medium. The formulation is carried out in a solution buffered to a pH compatible with the human body (since the hydrogel in question is generally intended for injection into the human body), said pH being between 6.5 and 7.5, advantageously between 7 and 7.4 and very advantageously between 7.1 and 7.3. The crosslinked polymer is in equilibrium in said solution. It also acquires an osmolarity compatible with that of the human body. Surprisingly, after this formulation step, the diluted crosslinked polymers of the invention are monophase hydrogels.

In one preferred variant of carrying out the invention, an injectable hydrogel of the invention is prepared by crosslinking a mixture of at least one polymer consisting of hyaluronic acid salt(s) (see above), neutralizing the crosslinked product obtained, and then formulating it into a solution buffered to a pH of between 7.1 and 7.3, at a concentration of between 10 and 40 mg/g, advantageously of between 20 and 30 mg/g.

The process for the preparation of the injectable monophase hydrogel from the crosslinked polymer (obtained by the crosslinking process constituting the first subject of the present invention) constitutes the second subject of the present invention.

We now come to the third and fourth subjects, which respectively consist of the crosslinked polymer obtainable after carrying out the crosslinking process (first subject), and the injectable monophase hydrogel obtainable by the formulation (second subject) of said crosslinked polymer, as stated above.

Said polymer and hydrogel advantageously contain low-molecular weight sodium hyaluronate and high-molecular weight sodium hyaluronate, the proportion of said low-molecular weight sodium hyaluronate very advantageously being more than 50% by weight.

The structure of the injectable monophase hydrogel—fourth subject of the present invention—is novel. Its consistency is resistant to degradation. This resistance of the hydrogel is far greater than that of the equivalent products of the prior art.

Those skilled in the art are aware that one of the methods of estimating the consistency of a hydrogel, especially of this type, is to measure the following parameter:

$$\tan. \text{ delta} = \frac{G''}{G'} = f(\text{stressing frequency}).$$

The hydrogels of the invention have the outlets indicated in the introduction of the present text. They are found to be particularly efficient for these purposes.

BRIEF DESCRIPTION OF THE DRAWINGS

In the drawing:
The FIGURE shows the curve tan.delta=f (stressing frequency) for each of the four hydrogels prepared according to Examples 1 to 4.

DETAILED DESCRIPTION OF THE PRESENTLY PREFERRED EMBODIMENTS

It is now proposed to illustrate the invention in its various features by means of the Examples below. More precisely:
Example 1 illustrates the prior art (crosslinking of a polymer of high molecular weight);
Example 2 illustrates the remarks made in the introduction of the present text (crosslinking of the same polymer of low molecular weight); and
Examples 3 and 4 illustrate the invention (crosslinking of the same polymer of low and high molecular weight, used in different relative amounts).
These are preceded by a description of a few methods of measurement used to characterize the products in question.
Measurement of the Intrinsic Viscosity
The intrinsic viscosity of sodium hyaluronate (NaHA) (in ml/g) is determined according to the European Pharmacopeia for NaHA (2.2.9) using a capillary viscometer of the Ubbelohde type.

Measurement of the Ejection Force (No Specific Standard for this Test)

The injectability of the gel based on NaHA is determined by measuring the force (in Newtons, N) required to eject the gel contained in a standard syringe, through a needle of 27 G½, at a rate of 12.5 mm/min. The tests were performed on a Verstatet® tensile device marketed by Mecmesin.

Measurement of the Remanence

The consistency of the gel is characterized at 25° C. by rheological measurement of the moduli of elasticity (G') and viscosity (G") as a function of the frequency (from 0.05 to 10 Hz), in the constant deformation domains, using a controlled stress rheometer (Carrimed CSL 500 from TA Instruments) and a cone-and-plate geometry of 4 cm 2°. This rheometer is checked and calibrated regularly. Degradation of the crosslinked gel results in a change in its consistency, which is measured by the increase in the parameter tangent delta (tan.delta=G"/G') as a function of time, at a frequency of 1 Hz. The gels are degraded by being heated to a temperature of 93° C. The time after which tan.delta reaches a value of 0.65 (corresponding to a degraded gel state) is measured at this temperature. A remanence index of 1 (corresponding to said time) was arbitrarily set for the gel of Example 1. The remanence index values indicated for the other gels are relative values.

Appearance of the Hydrogel

Monophase

Microscopic appearance: no apparent liquid phase—fine fragmentation of the gel into facets Macroscopic appearance: soft and free-flowing Biphase Microscopic appearance: gel fragments bathed in a low-viscosity liquid medium Macroscopic appearance: "purée" that fragments very easily—no cohesion of the gel and no free-flowing appearance Example 1

High-Molecular Weight Fibers 3.5 g of sodium hyaluronate (NaHa) Fibers of Intrinsic Viscosity 2800 ml/g and moisture content 8.7% are weighed out and 25.6 g of 0.25 N NaOH are added. Hydration of the fibers takes 2 h with regular manual homogenization using a spatula. 0.96 g of a solution of 1,4-butanediol diglycidyl ether (BDDE) diluted to ⅕ in 0.25 N sodium hydroxide solution is added to the reaction medium, this being followed by mechanical homogenization for 15 min before immersion in a thermostatically controlled bath at 50° C.±1° C.

$R=[BDDE]_0/[NaHA]_0=6\%$; $[NaHA]_i=105$ mg/g

The reaction takes 2 h. The crosslinked product is neutralized to pH 7.2 in a phosphate buffer solution and then dialyzed. The concentration of the resulting hydrogel is then adjusted ($[NaHA]_f=26$ mg/g) and the hydrogel is mechanically homogenized before being packed into syringes and sterilized in an autoclave by means of moist heat.

Injection force after sterilization: 25 N
Remanence index of the hydrogel: 1.0
Monophase hydrogel Example 2

Low-Molecular Weight Fibers 1.56 g of sodium hyaluronate (NaHA) fibers of intrinsic viscosity 600 ml/g and moisture content 5.5% are weighed out and 7.15 g of 0.25 N NaOH are added. Hydration of the fibers takes 2 h with regular manual homogenization using a spatula. 0.31 g of a solution of 1,4-butanediol diglycidyl ether (BDDE) diluted to ⅕ in 0.25 N sodium hydroxide solution is added to the reaction medium, this being followed by mechanical homogenization for 15 min before immersion in a thermostatically controlled bath at 50° C.±1° C.

$R=[BDDE]_0/[NaHA]_0=6.8\%$; $[NaHA]_i=174$ mg/g

The reaction takes 2 h. The crosslinked product is neutralized to pH 7.2 in a phosphate solution and then dialyzed. The concentration of the resulting hydrogel is then adjusted ($[NaHA]_f=26$ mg/g) and the hydrogel is mechanically homogenized before being packed into syringes and sterilized in an autoclave.

Injection force after sterilization: 24 N
Remanence index of the hydrogel: 6.0
Biphase hydrogel Example 3

Mixture of Fibers 0.763 g of sodium hyaluronate (NaHA) fibers of intrinsic viscosity 600 ml/g and moisture content 5.5% and 0.237 g of sodium hyaluronate fibers of intrinsic viscosity 2800 ml/g and moisture content 9.3% are weighed out. Proportions by weight in the mixture: 600/2800:77/23 (w/w).

The procedure remains identical to that of Example 2.

$R=[BDDE]_0/[NaHA]_0=7\%$; $[NaHA]_i=140$ mg/g; $[NaHA]_f=26$ mg/g

Injection force after sterilization: 15 N
Remanence index of the hydrogel: 3.6
Monophase hydrogel Example 4

Mixture of Fibers

The experiment of Example 3 is repeated, modifying the proportions by weight. Proportions by weight in the mixture: 600/2800:90/10 (w/w).

The procedure is identical to that of Example 2.

$R=[BDDE]_0/[NaHA]_0=6.5\%$; $[NaHA]_i=140$ mg/g; $[NaHA]_f=26$ mg/g

Injection force after sterilization: 14 N
Remanence index of the hydrogel: 7.7
Monophase hydrogel Said Examples are summarized in the Table below.

TABLE

| n° | $\eta_{int.}$ (ml/g) % = proportion by weight in mixture | $R = m_{BDDE}/m_{NaHA}$ | $[NaHA]_0$ mg/g | $[NaHA]_f$ in final gel mg/g | Appearance* | G', G", tan.delta (1 Hz) | $F_{ap\,ster}$ 27 G½ | Remanence index |
|---|---|---|---|---|---|---|---|---|
| 1 | (100%) 2800 | 6% | 105 | 26 | M | 143/65/0.40 | 25 | |
| 2 | (100%) 600 | 6.8% | 174 | 26 | B | 1300/100/0.08 | 24 | |

TABLE-continued

| | | | | | | | |
|---|---|---|---|---|---|---|---|
| 3 | (77%) 600 + (23%) 2800 | 7 | 140 | 26 | M | 262/27/0.10 | 15 |
| 4 | (90%) 600 + (10%) 2800 | 6.5 | 140 | 26 | M | 571/41/0.07 | 14 |

[NaHA]$_0$ = concentration of NaHA in the reaction medium at $t_0$
[NaHA]$_f$ = concentration of NaHA in the final hydrogel after reaction and dilution with a sufficient amount of phosphate buffer
G': modulus of elasticity of the final hydrogel (Pa · s) ⎫
G'': modulus of viscosity of the final hydrogel (Pa · s) ⎬ Carrimed CSL 500 rheometer
Tan.delta = G''/G' ⎭
$\eta_{int}$: intrinsic viscosity of the NaHA fiber/Ubbelohde viscometer
F: ejection force of the gel in N through a 27 G½ needle/100 N dynamometer
*M = monophase B = biphase The attached FIGURE shows the following curve:
Tan.delta=f (stressing frequency) for each of the four hydrogels prepared according to Examples 1 to 4.

The rheological behavior of the hydrogels of the invention (Examples 3 and 4) is different from that of the hydrogel of the prior art (Example 1).

Furthermore, the hydrogels of the invention are monophase and thus very different from the hydrogel of Example 2 (biphase).

What is claimed:

1. An injectable polymeric composition prepared by a process comprising the steps of:
   1) forming a mixture of a first hyaluronic acid salt having a first molecular weight of about $3 \times 10^5$ Da and a second hyaluronic acid salt having a second molecular weight of about $3 \times 10^6$ Da; and
   2) cross-linking the mixture formed in step 1) in an aqueous solvent in the presence of an effective and non-excessive amount of at least one cross-linking agent; and wherein the mixture contains about 90% by weight of the first hyaluronic acid salt and about 10% by weight of the second hyaluronic acid salt.

2. The composition of claim 1, wherein at least one of the first hyaluronic acid salt and second hyaluronic acid salt is selected from a sodium salt, a potassium salt, and mixtures thereof.

3. The composition of claim 1, wherein the cross-linking agent is selected from epichlorohydrin, divinyl sulfone, 1,4-bis(2,3-epoxypropoxy) butane, 1,2-bis(2,3-epoxypropoxy) ethylene, 1-(2,3-epoxypropyl)-2,3-epoxycyclohexane, aldehydes, and mixtures thereof.

4. The composition of claim 3, wherein the aldehydes are selected from formaldehyde, glutaraldehyde, crotonaldehyde, and mixtures thereof.

5. The composition of claim 1, wherein the cross-linking agent is 1,4-butanediol diglycidyl ether (BDDE).

6. The composition of claim 1, having a hyaluronic acid concentration of between 20 and 30 mg/g.

7. The composition of claim 1 having a hyaluronic acid concentration of between 10 and 40 mg/g.

8. The composition of claim 1 wherein the process further comprises the step of 3) formulating the mixture formed in step 2), into a solution buffered to a pH of between 6.5 and 7.5.

9. The composition of claim 8, wherein the pH is between 7 and 7.4.

10. The composition of claim 8, wherein the pH is between 7.1 and 7.3.

11. The composition of claim 1 wherein the degree of crosslinking in the mixture is between 4% and 50%.

12. The composition of claim 1 wherein the mixture has an intrinsic viscosity of less than 1900 ml/g.

13. The composition of claim 1, wherein each of the first hyaluronic acid salt and second hyaluronic acid salt is a sodium salt.

* * * * *

UNITED STATES PATENT AND TRADEMARK OFFICE
CERTIFICATE OF CORRECTION

PATENT NO. : 8,338,388 B2
APPLICATION NO. : 12/782488
DATED : December 25, 2012
INVENTOR(S) : Pierre Lebreton It is certified that error appears in the above-identified patent and that said Letters Patent is hereby corrected as shown below:

On the Title page, Item (56), in column 2, under "Other Publications", line 3, delete "Antiibrosis" and insert -- Antifibrosis --, therefor.

On the Title page, Item (56), in column 2, under "Other Publications", line 3, delete "Slerotomy" and insert -- Sclerotomy --, therefor.

On the Title page, Item (56), in column 2, under "Other Publications", line 12, delete "Anesthesiol" and insert -- Anaesthesiol --, therefor.

On the Title page, Item (56), in column 2, under "Other Publications", line 14, delete "Carbodimide,"" and insert -- Carbodiimide," --, therefor.

On Title page 3, Item (56), in column 1, under "Other Publications", line 3, delete "Hyaluroinic" and insert -- Hyaluronic --, therefor.

On Title page 3, Item (56), in column 1, under "Other Publications", line 15, delete "(JUVADERM)" and insert -- (JUVEDERM) --, therefor.

On Title page 3, Item (56), in column 2, under "Other Publications", line 10, delete "Chrondrocytes" and insert -- Chondrocytes --, therefor.

On Title page 3, Item (56), in column 2, under "Other Publications", line 42, delete "Gonarthosis:" and insert -- Gonarthrosis: --, therefor.

On Title page 3, Item (56), in column 2, under "Other Publications", line 52, delete "An Theum Dis;" and insert -- Ann Rheum Dis; --, therefor.

On Title page 4, Item (56), in column 1, under "Other Publications", line 19, delete "Rheuymatism;" and insert -- Rheumatism; --, therefor.

Signed and Sealed this
Twenty-third Day of September, 2014

Michelle K. Lee
*Deputy Director of the United States Patent and Trademark Office*

CERTIFICATE OF CORRECTION (continued)
U.S. Pat. No. 8,338,388 B2

On Title page 4, Item (56), in column 1, under "Other Publications", line 20, delete "Evlaution" and insert -- Evaluation --, therefor.

On Title page 4, Item (56), in column 1, under "Other Publications", line 22, delete "Chartacterization"; Plastric" and insert -- Characterization"; Plastic --, therefor.

On Title page 4, Item (56), in column 2, under "Other Publications", line 9, delete "Viscoelstic" and insert -- Viscoelastic --, therefor.

On Title page 4, Item (56), in column 2, under "Other Publications", line 9, delete "htt://" and insert -- http:// --, therefor.

On Title page 4, Item (56), in column 2, under "Other Publications", line 46, delete ""Influcence" and insert -- "Influence --, therefor.

On Title page 4, Item (56), in column 2, under "Other Publications", line 47-48, delete "Chemcio-Biological" and insert -- Chemico-Biological --, therefor.

On Title page 4, Item (56), in column 2, under "Other Publications", line 52, delete "etal" and insert -- et al. --, therefor.

On Title page 4, Item (56), in column 2, under "Other Publications", line 53, delete "Crosslinkedwith" and insert -- Crosslinked with --, therefor.

On Title page 4, Item (56), in column 2, under "Other Publications", line 53-54, delete "Glyol Tetracrylates";" and insert -- Glycol Tetraacrylate"; --, therefor.

In the Specification

In column 2, line 60, delete "Da,$\approx 2.10^6$" and insert -- Da, $\approx 2.10^6$ --, therefor.

In column 7, line 40, delete "(NaHa)" and insert -- (NaHA) --, therefor.

In the Claims

In column 10, line 14, in claim 3, delete "epoxypropyl) -2,3" and insert -- epoxypropyl)-2,3 --, therefor.

UNITED STATES PATENT AND TRADEMARK OFFICE
CERTIFICATE OF CORRECTION

PATENT NO. : 8,338,388 B2  
APPLICATION NO. : 12/782488  
DATED : December 25, 2012  
INVENTOR(S) : Pierre F. Lebreton Page 1 of 1

It is certified that error appears in the above-identified patent and that said Letters Patent is hereby corrected as shown below:

On the title page, first column, item (73), delete "Allergan, Inc., Irvine, CA (US)" and insert -- Allergan Industrie, SAS (FR) --, therefor.

Signed and Sealed this
Twenty-second Day of September, 2015

Michelle K. Lee
*Director of the United States Patent and Trademark Office*